(12) United States Patent
Berry (10) Patent No.: US 11,589,904 B2
(45) Date of Patent: Feb. 28, 2023

(54) PEDICLE SCREW WITH DETACHABLE POLYAXIAL HEAD

(71) Applicant: Bret Michael Berry, Tallahassee, FL (US)

(72) Inventor: Bret Michael Berry, Tallahassee, FL (US)

( * ) Notice: Subject to any disclaimer, the term of this patent is extended or adjusted under 35 U.S.C. 154(b) by 0 days.

(21) Appl. No.: 17/219,828

(22) Filed: Mar. 31, 2021

(65) Prior Publication Data

US 2022/0313321 A1 Oct. 6, 2022

(51) Int. Cl.
*A61B 17/70* (2006.01)

(52) U.S. Cl.
CPC ................................ *A61B 17/7037* (2013.01)

(58) Field of Classification Search
CPC .................. A61B 17/70; A61B 17/7032–7046
See application file for complete search history.

(56) References Cited

U.S. PATENT DOCUMENTS

| 6,368,321 | B1 * | 4/2002 | Jackson | A61B 17/7032 606/272 |
| 9,517,089 | B1 * | 12/2016 | Casey | A61B 17/7041 |
| 2006/0116677 | A1 * | 6/2006 | Burd | A61B 17/7076 606/270 |
| 2007/0093819 | A1 * | 4/2007 | Albert | A61B 17/70 606/278 |
| 2008/0147121 | A1 * | 6/2008 | Justis | A61B 17/7037 606/246 |
| 2009/0082812 | A1 * | 3/2009 | Lewis | A61B 17/7041 606/103 |
| 2014/0088650 | A1 * | 3/2014 | Taddia | A61B 17/7032 606/267 |
| 2017/0086885 | A1 * | 3/2017 | Duncan | A61B 17/7041 |

* cited by examiner

*Primary Examiner* — Eduardo C Robert
*Assistant Examiner* — Michelle C Eckman
(74) *Attorney, Agent, or Firm* — Ellenoff Grossman & Schole LLP; James M. Smedley; Alex Korona (57) ABSTRACT

A pedicle screw device for fixating at least two adjacent vertebral bodies is presented. The device consists of a bone screw which is implanted into the pedicle of a vertebral body. A second bone screw is implanted into the pedicle of a second vertebral body. A polyaxial head is then inserted over each bone screw. The polyaxial heads can then be slid into a retaining position on the bone screw, allowing them to rotate about the spherical portion of the bone screw. The polyaxial heads are then attached to one another with a rod. Finally, a locking screw is inserted into the polyaxial heads to force the rod against the bone screw as well as the polyaxial head, locking them in place. The rod also serves to prevent the polyaxial head from disconnecting from the bone screw.

16 Claims, 7 Drawing Sheets

PEDICLE SCREW WITH DETACHABLE POLYAXIAL HEAD

FIELD OF INVENTION

The present invention relates to a pedicle screw implant assembly, and more particularly, a pedicle screw with an offset and removable polyaxial head.

BACKGROUND OF INVENTION

While certain existing pedicle screws include detachable, or modular, polyaxial heads, those pedicle screws with detachable heads generally rely on the detachable head being axial to the bone screw body. In particular, existing detachable heads are generally attached either by threading the polyaxial head onto the pedicle screw, or by means of an expandable portion, either in the polyaxial head itself, or by means of a collet.

There are significant drawbacks to both of these methods. First, threading a polyaxial head over a screw can result in merely driving the bone screw further into pedicle, which can have seriously dangerous consequences, such as driving the screw through the anterior wall of the vertebral body. Also, threading a polyaxial head over a screw could also lead to seating the bone screw too deep into the pedicle, thereby preventing the polyaxial head from properly seating onto the bone screw. Furthermore, threading a polyaxial head over a screw can cause the threads on the bone screw head to deform during tightening, thereby preventing proper rigid fixation.

Similarly, there are disadvantages in using a collet as an attachment mechanism to secure a polyaxial head to a bone screw. A collet is able to connect over a bone screw, because the collet elastically deforms open during attachment of the polyaxial head to the bone screw head, thereby relying on the elasticity of the metal to return to its original shape and size to secure to the bone screw head. While this can create an attachment, it also creates a weak point, as the collet can reopen unexpectedly. Typically, this happens when the collet and bone screw head are not properly seated together or can happen when soft tissue impedes proper seating. Moreover, collets are known to become unseated from the bone screw head even after the entire construct is locked in place, including after surgery, when the forces of the spine act to pull the rod and polyaxial head away from the bone screw, resulting in a failed fusion and the need for a second surgery.

Therefore, there is a need in the art for a pedicle screw system with a polyaxial head that can be attached to the screw head by a means other than by threading the head onto the bone screw or through attachment via a collet. These and other features and advantages of the present invention will be explained and will become obvious to one skilled in the art through the summary of the invention that follows.

SUMMARY OF THE INVENTION

Accordingly, it is an aspect of the present invention to provide a pedicle screw system configured with a polyaxial head that attaches under the bottom of the head of the bone screw and is configured to receive the head of the bone screw in a cavity formed in the polyaxial head. The polyaxial head is further configured with a channel that receives a fusion rod and a threaded portion that receives locking screw, with the fusion rod channel being formed continuously with the cavity that receives the head of the bone screw. Collectively, the fusion rod and locking screw operate to secure the head of the bone screw with the cavity.

According to an embodiment of the present invention, a pedicle implant assembly comprising a polyaxial head comprising a vertical screw head channel formed within a first lateral side of the polyaxial head, a spherical screw head aperture formed within a second lateral side of the polyaxial head, and a horizontal screw head channel connecting between the vertical screw head channel and the spherical screw head aperture.

According to an embodiment of the present invention, the pedicle implant assembly further comprises a bone screw formed with a spherical head, a neck portion, and a threaded portion.

According to an embodiment of the present invention, the neck of the bone screw is narrower than the spherical head and threaded portion of the bone screw.

According to an embodiment of the present invention, the pedicle implant assembly further comprises a pair of retaining tabs, wherein the pair of retaining tabs are positioned between the horizontal screw head channel and the spherical screw head aperture.

According to an embodiment of the present invention, the pair of retaining tabs are configured to flex outward when a head portion of a bone screw is moved between the horizontal screw head channel and the spherical screw head aperture.

According to an embodiment of the present invention, the pedicle implant assembly further comprises a screw neck aperture formed in a bottom face of the polyaxial head.

According to an embodiment of the present invention, the screw neck aperture terminates at, and is formed continuously with, a bone screw opening formed at the first lateral side of the polyaxial head.

According to an embodiment of the present invention, the pedicle implant assembly further comprises a rod slot formed within the first lateral side of the polyaxial head.

According to an embodiment of the present invention, the rod slot is open at a top side of the polyaxial head and is formed with a threaded portion at a top edge of the rod slot.

According to an embodiment of the present invention, the rod slot and the vertical screw head channel share a center axis.

According to an embodiment of the present invention, a pedicle implant assembly comprising a polyaxial head comprising a vertical screw head channel formed within a first lateral side of the polyaxial head, a spherical screw head aperture formed within a second lateral side of the polyaxial head, a horizontal screw head channel connecting between the vertical screw head channel and the spherical screw head aperture, and a pair of retaining tabs configured to retain a bone screw within the spherical screw head, wherein the pair of retaining tabs are aligned on opposite walls of the polyaxial head and between the spherical screw head aperture and the horizontal screw head channel.

According to an embodiment of the present invention, the bone screw is formed with a spherical head, a neck portion, and a threaded portion and the neck portion of the bone screw is narrower than the spherical head and threaded portion of the bone screw.

According to an embodiment of the present invention, the pair of retaining tabs are configured to flex outward from the horizontal screw head channel as the spherical head of the bone screw is moved from the horizontal screw head channel into the spherical screw head aperture.

According to an embodiment of the present invention, the pedicle implant assembly further comprises a screw neck aperture formed in a bottom face of the polyaxial head, wherein the screw neck aperture is wider than the neck portion of the bone screw and narrower than the spherical head of the bone screw.

According to an embodiment of the present invention, the vertical screw head channel intersects with the screw neck aperture at the first lateral side of the polyaxial head and is configured to accommodate the spherical head of the bone screw.

According to an embodiment of the present invention, the pedicle implant assembly further comprises a rod slot formed within the first lateral side of the polyaxial head, wherein a lateral sidewall of the rod slot is formed continuously with a lateral sidewall of the vertical screw head channel and a medial sidewall of the rod slot terminates at the screw head aperture.

According to an embodiment of the present invention, a pedicle implant assembly comprising a pedicle implant assembly comprising a bone screw formed with a spherical head, a neck portion, and a threaded portion, wherein the neck of the bone screw is narrower than the spherical head and threaded portion of the bone screw; and a polyaxial head a comprising a screw neck aperture formed in a bottom face of the polyaxial head and a vertical channel opening formed in the bottom face of the polyaxial head, wherein the screw neck aperture is narrower than the spherical head of the bone screw and the vertical channel opening is wider than the spherical head of the bone screw.

According to an embodiment of the present invention, the pedicle implant assembly further comprises a spherical screw head aperture formed in the polyaxial head above an end of the screw neck aperture that is opposite the vertical channel opening and a horizontal screw head channel formed continuously with, and extending away from, the spherical screw head aperture toward the vertical channel opening.

According to an embodiment of the present invention, the pedicle implant assembly further comprises a pair of retaining tabs, wherein the pair of retaining tabs are positioned between the horizontal screw head channel and the spherical screw head aperture.

According to an embodiment of the present invention, the pedicle implant assembly further comprises a vertical screw head channel extending from a top face of the polyaxial head and terminating at the vertical channel opening.

The foregoing summary of the present invention with the preferred embodiments should not be construed to limit the scope of the invention. It should be understood and obvious to one skilled in the art that the embodiments of the invention thus described may be further modified without departing from the spirit and scope of the invention.

DETAILED DESCRIPTION

In the Summary above and in this Detailed Description, and the claims below, and in the accompanying drawings, reference is made to particular features of various embodiments of the invention. It is to be understood that the disclosure of embodiments of the invention in this specification includes all possible combinations of such particular features. For example, where a particular feature is disclosed in the context of a particular aspect or embodiment of the invention, or a particular claim, that feature can also be used—to the extent possible—in combination with and/or in the context of other particular aspects and embodiments of the invention, and in the invention generally. It should be noted that the features illustrated in the drawings are not necessarily drawn to scale and descriptions of well-known components and techniques may be omitted so as to not unnecessarily obscure the embodiments.

While multiple embodiments are disclosed, still other embodiments of the present invention will become apparent to those skilled in the art from this detailed description. The invention is capable of myriad modifications in various obvious aspects, all without departing from the spirit and scope of the present invention. Accordingly, the drawings and descriptions are to be regarded as illustrative in nature and not restrictive.

In accordance with embodiments of the present invention, a pedicle screw implant assembly disclosed herein is configured to fix two adjacent vertebrae. In a preferred embodiment, as depicted by at least FIGS. 1-7, the implant assembly 10 comprises at least two bone screws 20, each with a detachable, offset polyaxial head 30, with a bone screw 20 being implanted into each of two adjacent vertebrae V1, V2. The implant assembly 10, further comprises an elongated cylindrical rod 40 that connects the polyaxial heads 30 of the bones screws 20 together. Finally, locking screws 50 secure the rod 40 to the polyaxial heads 30 and thereby fixing the two adjacent vertebrae V1, V2 together.

Figure 10:
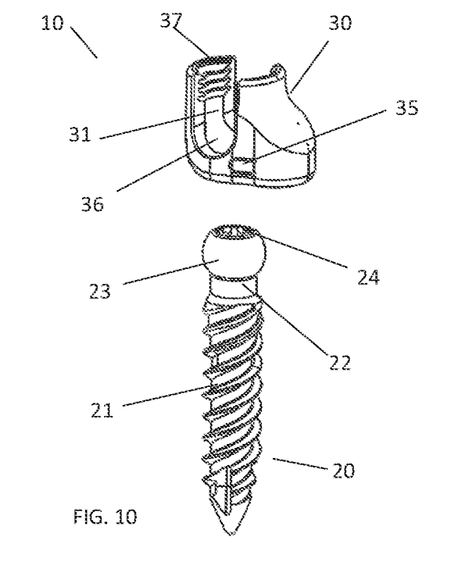
FIG. 10 is an exploded perspective view of a first preferred embodiment of a pedicle screw and polyaxial head assembly.
Figure 11:
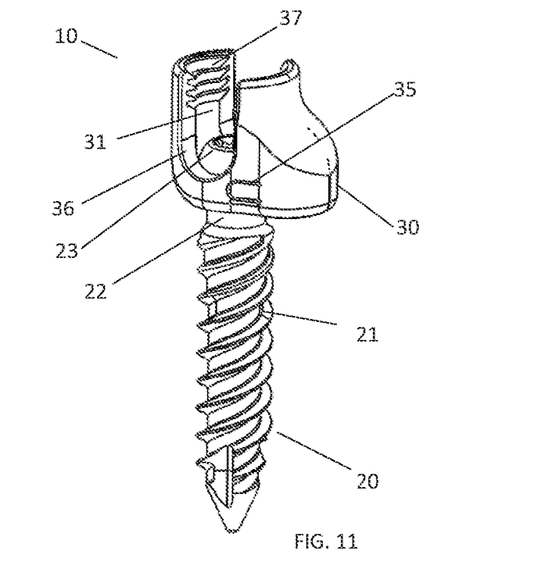
FIG. 11 is a perspective view of a first preferred embodiment of a pedicle screw and polyaxial head assembly with the polyaxial head mounted on the pedicle screw in an unsecured position.
Figure 13:
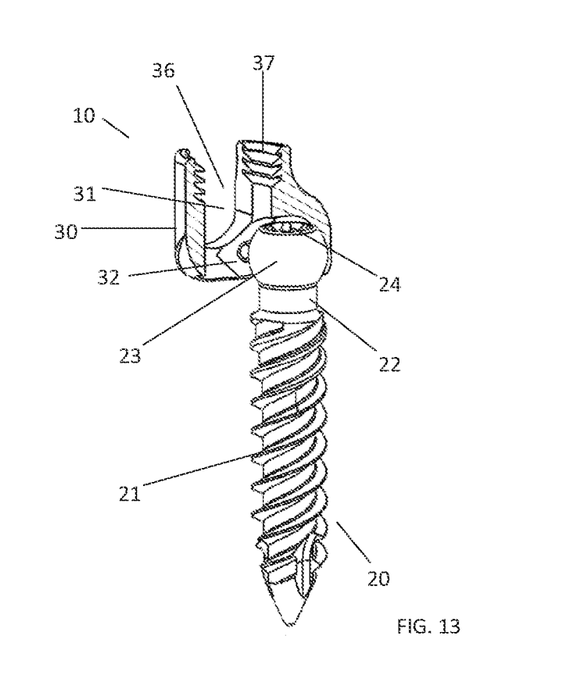
FIG. 13 is a perspective section view of a first preferred embodiment of a pedicle screw and polyaxial head assembly with the polyaxial head mounted on the pedicle screw in a fixed position.

In a preferred embodiment, as shown by at least FIG. 10 and FIG. 13, the bone screw 20 component is comprised of an elongated bone thread portion 21 that is configured to thread into and anchor to the vertebral body. At the proximal end of the bone thread portion 21, is cylindrical neck portion 22 that is relatively narrower than the other portions of the bone screw 20. Sitting atop the neck portion 22 is a spherical head 23, the diameter of which is larger than the neck 22. A drive feature 24 configured to receive a screw driver is formed inside of the spherical head 23.

Figure 1:
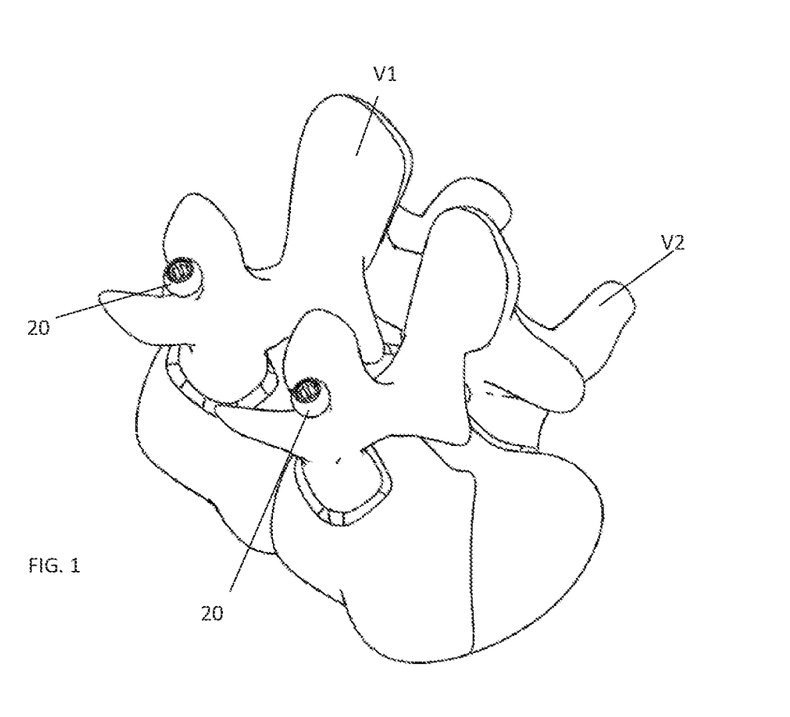
FIG. 1 is a perspective view of two adjacent of vertebrae with a pedicle screws implanted in each of the vertebrae.
Figure 2:
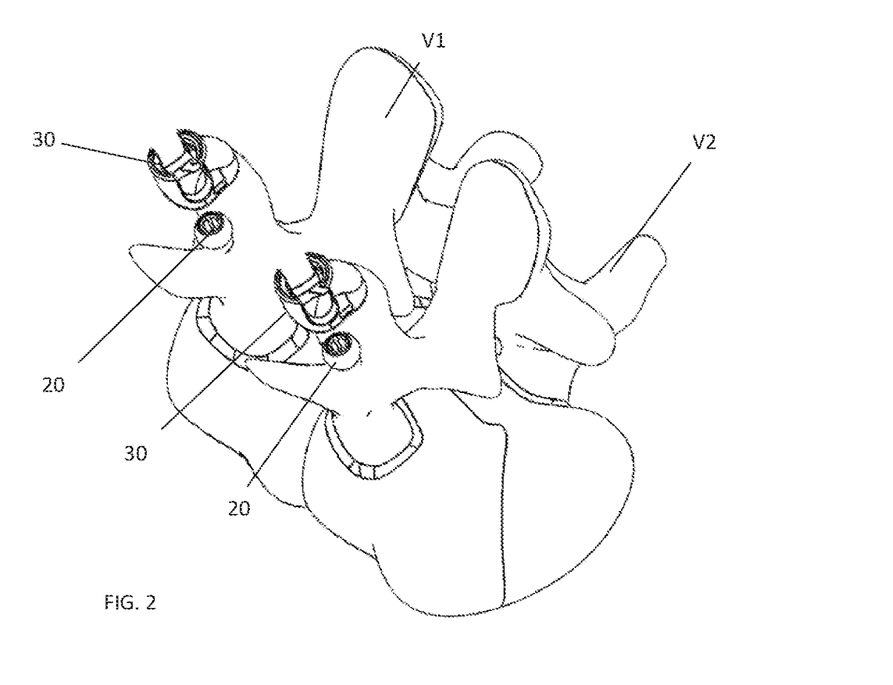
FIG. 2 is a perspective view of a first preferred embodiment of a polyaxial head being placed over a pedicle screw implanted in each of two adjacent vertebrae.
Figure 3:
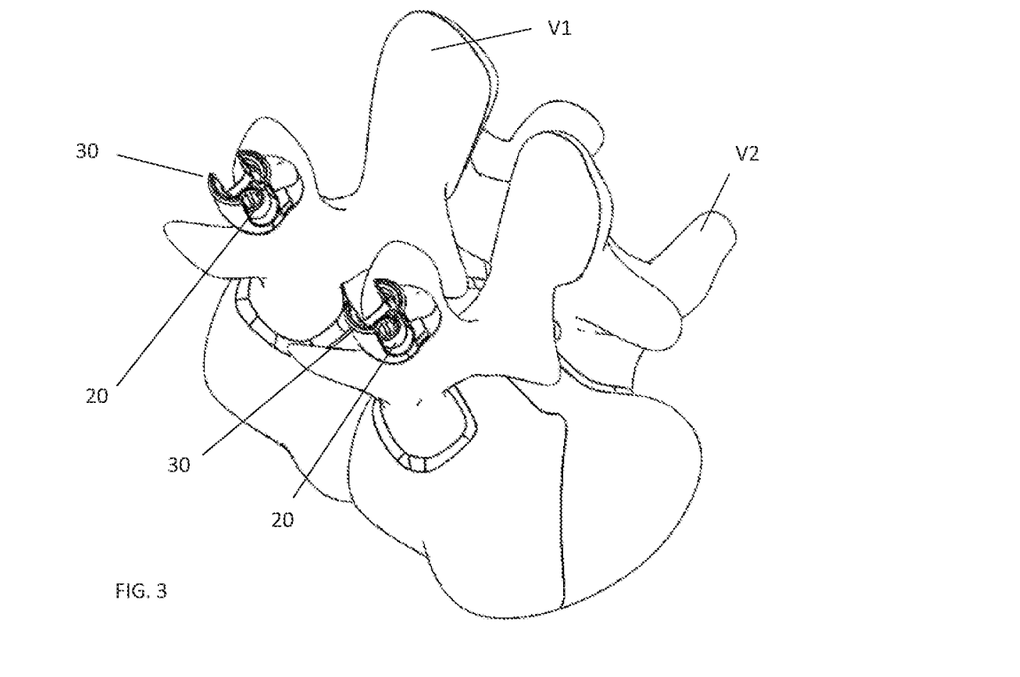
FIG. 3 is a perspective view of a first preferred embodiment of a polyaxial head attached in an unsecured position on a pedicle screw implanted in each of two adjacent vertebrae.
Figure 4:
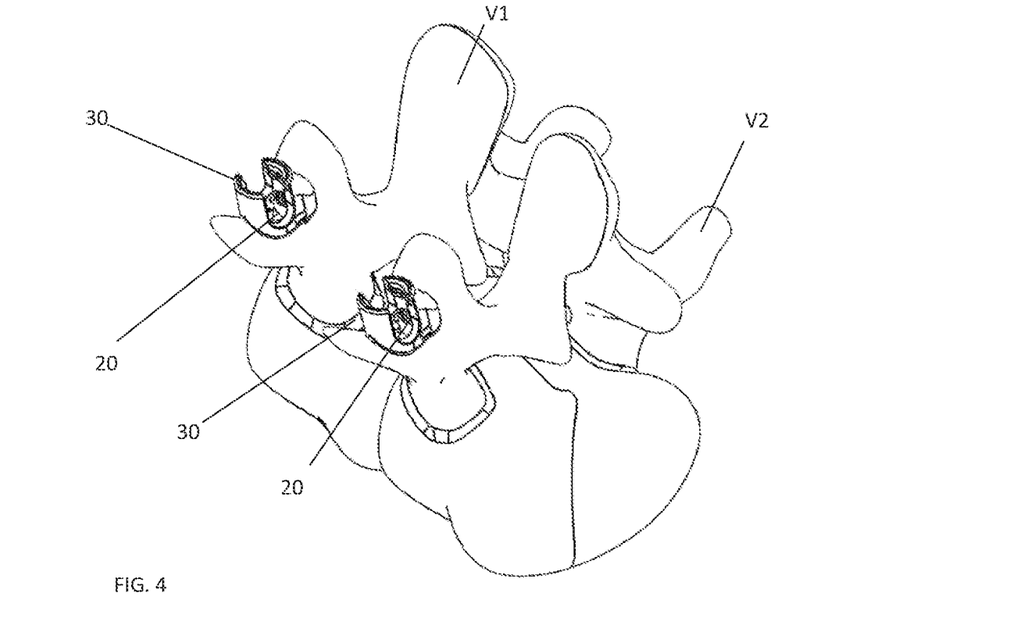
FIG. 4 is a perspective view of a first preferred embodiment of a polyaxial head attached in fixed position on a pedicle screw implanted in each of two adjacent vertebrae.

In a preferred embodiment, as best shown by FIGS. 1-3, at least one bone screw 20 is implanted into the pedicle of at least two adjacent vertebrae V1, V2. The bone screws 20 are inserted into the vertebrae V1, V2, so as to leave the neck 22 and spherical head 23 portions of the bone screws 20 exposed above the bone of the pedicle. A polyaxial head 30 component is then placed over the spherical head 23 of each bone screw 20.

In a preferred embodiment, as shown by at least FIGS. 10-13, the polyaxial head 30 is formed with a vertical screw head channel 31 running along the proximal-distal axis. In the preferred embodiment, the vertical screw head channel 31 is nominally the same diameter as the spherical head 23 of the bone screw 20. The vertical screw head channel 31 extends through the bottom face of the polyaxial head 30 creating an opening that is the full diameter of the vertical screw head channel 31. The opening of the vertical screw head channel 31 formed in the bottom face of the polyaxial head 30 may be continuous with, and define the terminus of the first end of, the screw neck aperture 34. To attach the polyaxial head 30 to the bone screw 20, the vertical screw head channel 31 of the polyaxial head 30 is slid over the spherical head 23 of bone screw 20.

When the polyaxial head 30 is in place over the bone screw 20 with the spherical head 23 within the vertical screw head channel 31, the polyaxial head 30 is in the unrestrained position or unsecured position, wherein there is no mechanism securely fastening the polyaxial head 30 together with the bone screw 20. The polyaxial head 30 is configured to slide over the spherical head 23 of the bone screw 20 so that the spherical head 23 slides within the horizontal screw head channel 32 polyaxial head 30. In a preferred embodiment, as shown by at least FIG. 12 and FIG. 13, the horizontal screw head channel 32 is nominally the diameter of spherical head 23 of the bone screw 20 and runs perpendicular to the vertical screw head channel 31. In the preferred embodiment, the center point of the horizontal screw head channel 32 is above the bottom face of the polyaxial head 30, such that the horizontal screw head channel 32 aligns with the screw neck aperture 34 formed in the bottom face of the polyaxial head 30.

Figure 14:
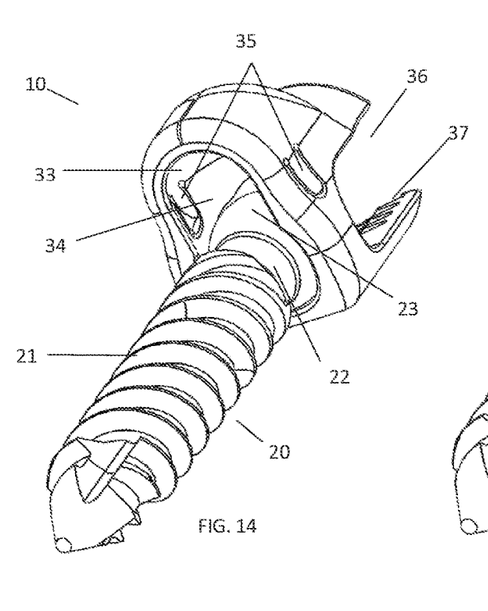
FIG. 14 is a lower perspective view of a first preferred embodiment of a pedicle screw and polyaxial head assembly with the polyaxial head mounted on bone screw in an unsecured position.
Figure 15:
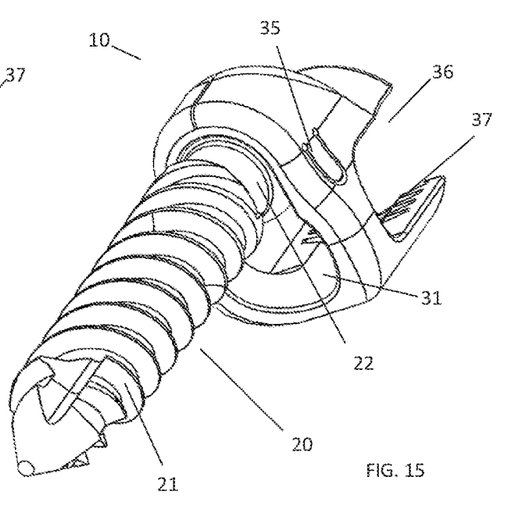
FIG. 15 is a lower perspective view of a first preferred embodiment of a pedicle screw and polyaxial head assembly with the polyaxial head mounted on bone screw in a fixed position.

In a preferred embodiment, as shown by at least FIG. 14 and FIG. 15, the screw neck aperture 34 has a width that is less than the width of spherical head 23 of the bone screw 20, but greater than the width of the neck 22 of the bone screw 20. This enables the polyaxial head 30 to slide horizontally over the bone screw 20, with the neck 22 passing through the screw neck aperture 34, while the spherical head 23 passes through the horizontal screw head channel 32. With the spherical head 23 being wider than the screw neck aperture 34, the polyaxial head 30 is prevented from being lifted off of the bone screw 20. As the polyaxial head 30 slides horizontally over the spherical head 23 of the bone screw 20 toward the spherical screw head aperture 33, the polyaxial head 30 remains in the unrestrained position or unsecured position. In the preferred embodiment, a first end of the screw neck aperture 34 terminates at the opening of the vertical screw head channel 31 formed in the bottom face of the polyaxial head 30 and a second end of the screw neck aperture 34 terminates below the spherical screw head aperture 33. In some embodiments, the opening of the vertical screw head channel 31 formed in the bottom face of the polyaxial head 30 may be continuous with the screw neck aperture 34, with the opening of the vertical screw head channel 31 being wider than the screw neck aperture 34 and thereby marking the boundary between the opening of the vertical screw head channel 31 and the screw neck aperture 34.

Figure 12:
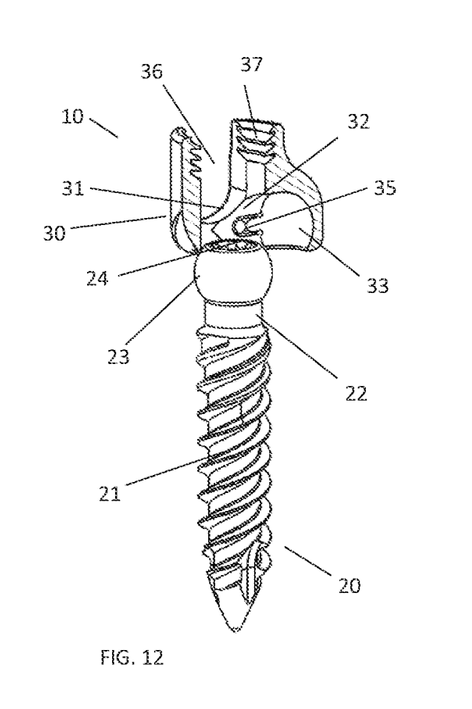
FIG. 12 a perspective section view of a first preferred embodiment of a pedicle screw and polyaxial head assembly with the polyaxial head mounted on the pedicle screw in an unsecured position.

In a preferred embodiment, as shown by least FIG. 12 and FIG. 13, the horizontal screw head channel 32 connects the vertical screw head channel 31 to the spherical screw head aperture 33 of the polyaxial head 30. In the preferred embodiment, the spherical screw head aperture 33 has the same center point and diameter as the horizontal screw head channel 32 and likewise aligns with the screw neck aperture 34 formed in the bottom face of the polyaxial head 30, such that the spherical screw head aperture 33 is above the terminal end of the screw neck aperture 34 that is opposite the vertical screw head channel 31 screw neck. Therefore, when the spherical head 23 of the bone screw is within the spherical screw head aperture 33 of the polyaxial head 30, the polyaxial head 30 cannot be lifting vertically off of the bone screw 20, but it can now rotate polyaxially about the spherical head 23 of the bone screw 20. Additionally, as the spherical head 23 of the bone screw 20 passes through the horizontal screw head channel 32 and into the spherical screw head aperture 33 of the polyaxial head 30, the spherical head 23 of the bone screw 20 passes and engages with the retaining tabs 35. With the spherical head 23 of the bone screw 20 being secured by the retaining tabs 35 within the spherical screw head aperture 33 of the polyaxial head 30, the polyaxial head 30 is in the restrained position or fixed position on the bone screw 20.

In a preferred embodiment, as shown by at least FIG. 12 and FIG. 14, the retaining tabs 35 are on the interior of the polyaxial head 30 and extend out into the horizontal screw head channel 32. The retaining tabs 35 are formed in the side walls of the polyaxial head 30 to allow the retaining tabs 35 to flex outward. In the preferred embodiment, the distance between the retaining tabs 35 is less than the diameter of the spherical head 23 of the bone screw 20. As the spherical head 23 of the bone screw 20 passes through the horizontal screw head channel 32, the spherical head 23 pushes the retaining tabs 35 outward. When the spherical head 23 of the bone screw 20 enters the spherical screw head aperture 33, the retaining tabs 35 flex back into a resting position. With the spherical head 23 of the bone screw 20 in the spherical screw head aperture 33 and the retaining tabs 35 flexed back into the resting position, the retaining tabs 35 thereby hold the spherical head 23 of the bone screw 20 within spherical screw head aperture 33 of the polyaxial head 30. In the preferred embodiment, the retaining tabs 35 alone are not intended to be a permanent retention mechanism or final means of securing the polyaxial head 30 onto bone screw 20, as a surgeon can, with nominal effort, apply sufficient force to overcome the retaining force of the retaining tabs 35 and thereby remove the polyaxial head 30 from bone screw 20 after reversing the spherical head 23 of the bone screw 20 back through horizontal screw head channel 32 and into vertical screw head channel 31. However, the retaining force provided by the retaining tabs 35 is sufficient to prevent the polyaxial head 30 from inadvertently disengaging from the bone screw 20 in situ, especially as the surgeon is generally position the various components of the overall construct.

Figure 5:
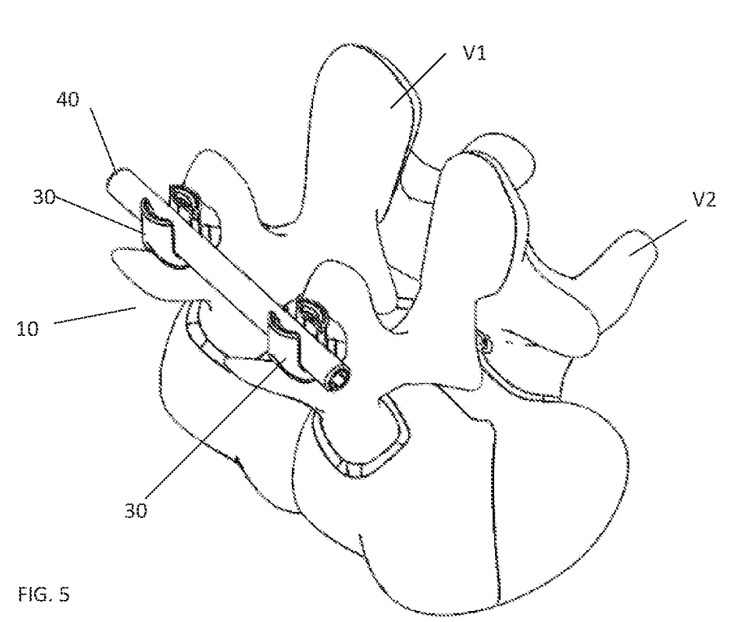
FIG. 5 is a perspective view of a rod being inserted between a first embodiment of a polyaxial head on each of two adjacent vertebrae.
Figure 6:
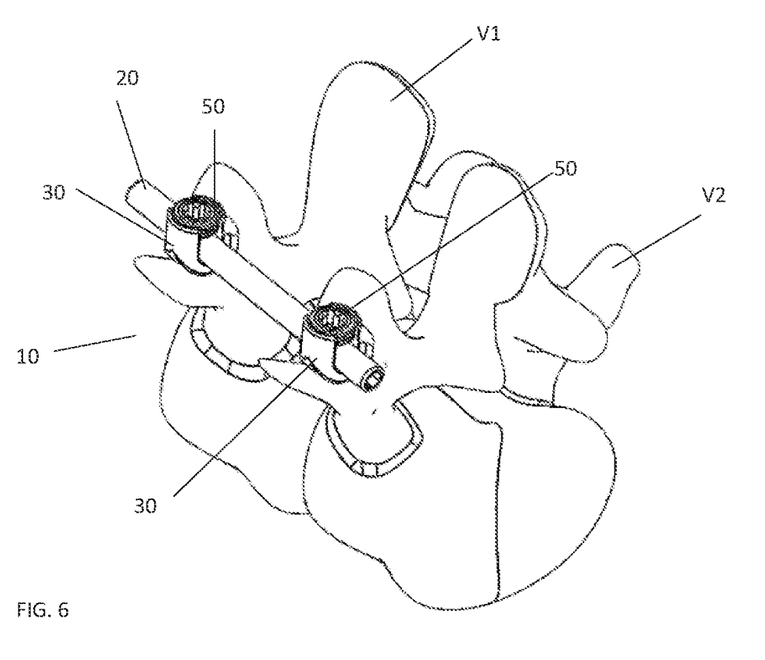
FIG. 6 is a perspective view of a locking screw fastening to a polyaxial head on each of two adjacent vertebrae in order to secure a rod within the polyaxial heads.
Figure 7:
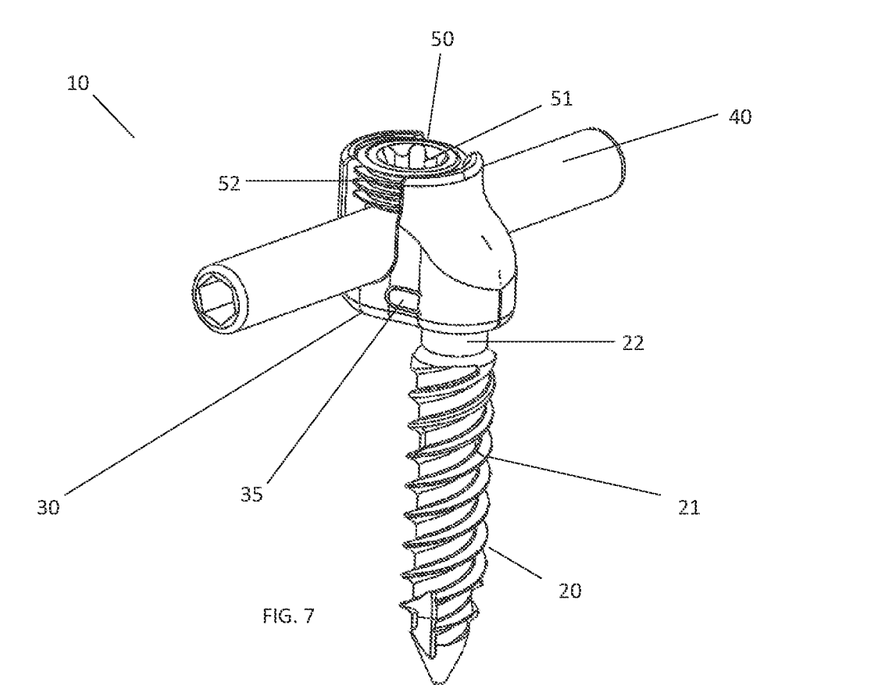
FIG. 7 is a perspective view of a first preferred embodiment of a pedicle screw and polyaxial head assembly.
Figure 8:
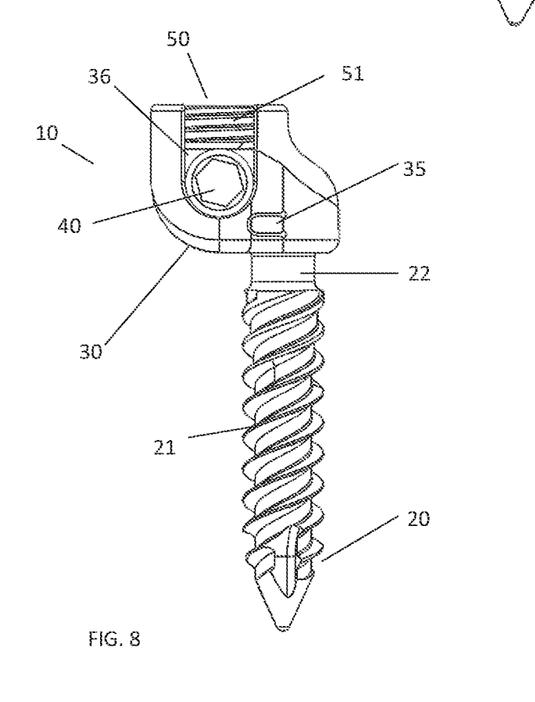
FIG. 8 is a side view of a first preferred embodiment of a pedicle screw and polyaxial head assembly.
Figure 9:
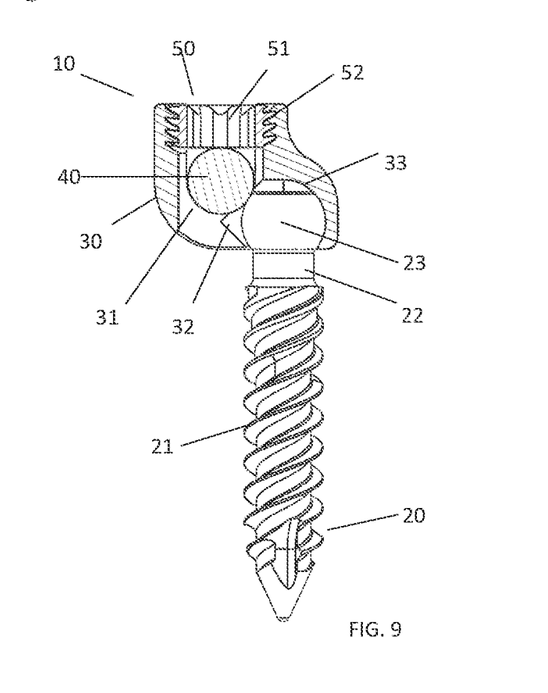
FIG. 9 is a sectioned side view of a first preferred embodiment pedicle screw and polyaxial head assembly with the pedicle screw unsectioned.
Figure 16:
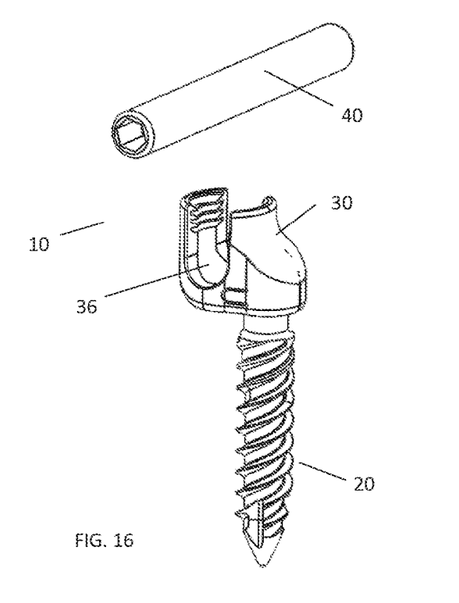
FIG. 16 is a perspective view of a first preferred embodiment of a pedicle screw and polyaxial head assembly depicting the insertion of a rod into the polyaxial head.
Figure 17:
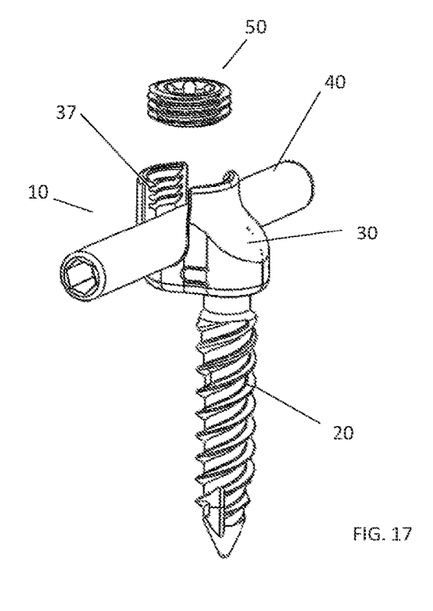
FIG. 17 is a perspective view of a first preferred embodiment of a pedicle screw and polyaxial head assembly depicting the fastening of a locking screw onto polyaxial head.
Figure 18:
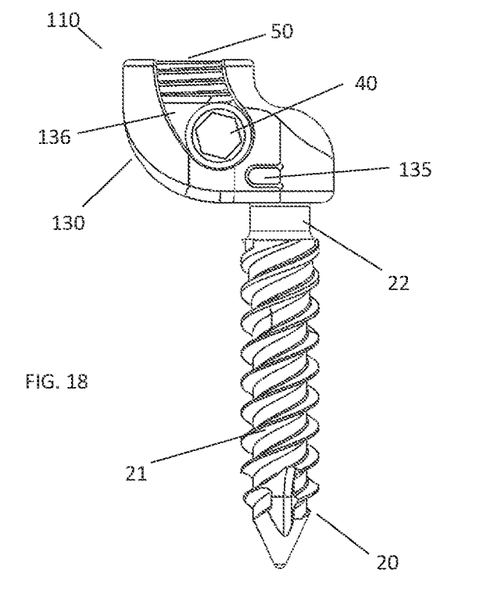
FIG. 18 is a side view of a second preferred embodiment of a pedicle screw and polyaxial head assembly.
Figure 19:
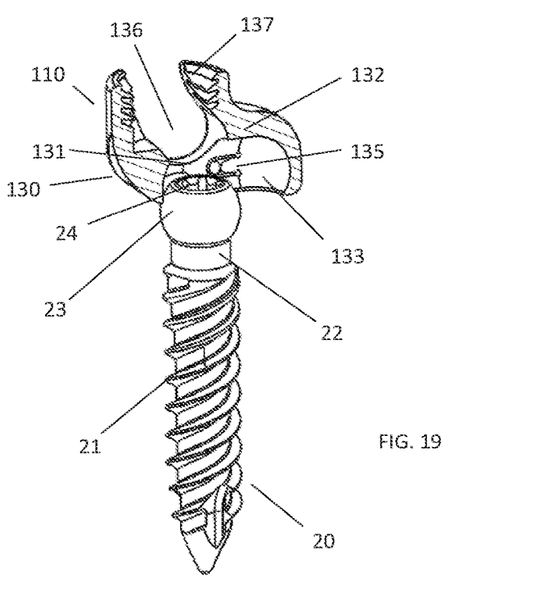
FIG. 19 a perspective section view of a second preferred embodiment of a pedicle screw and polyaxial head assembly with the polyaxial head mounted on the pedicle screw in an unsecured position.
Figure 20:
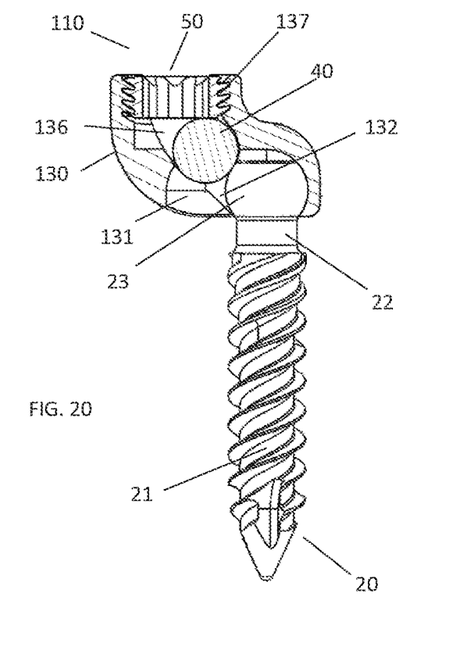
FIG. 20 is a sectioned side view of a second preferred embodiment pedicle screw and polyaxial head assembly with the pedicle screw unsectioned.
Figure 21:
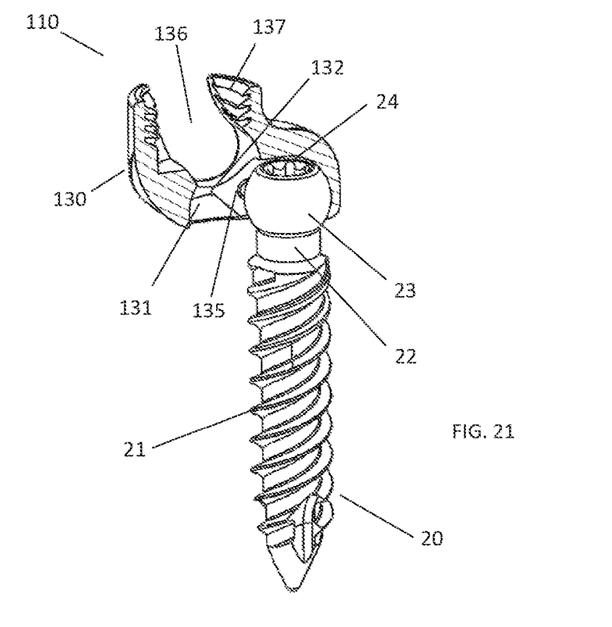
FIG. 21 is a perspective section view of a first preferred embodiment of a pedicle screw and polyaxial head assembly with the polyaxial head mounted on the pedicle screw in a fixed position.

In a preferred embodiment, as shown by at least FIG. 5 and FIG. 16, with the polyaxial head 30 in the retained position, the rod 40 can then be inserted into the rod slot 36 formed in the polyaxial head 30. In the preferred embodiment, the rod slot 36 forms an opening that extends cephalad-caudad across the polyaxial head 30. In the preferred embodiment, the rod slot 36 also extends from the upper or proximal face of the polyaxial screw head 30 to the spherical screw head aperture 33. This configuration, as shown by at least FIG. 9, allows the rod 40 to seat against the spherical head 23 of the bone screw 20. Furthermore, the rod 40 sitting in the rod slots 36 prevents the spherical head 23 of the bone screw 20 from moving back into the horizontal screw head channel 32, thereby preventing the polyaxial head 30 from disengaging from of the bone screw 20.

In a preferred embodiment, as shown by at least FIGS. 6-9 and FIG. 17, with the rod 40 in place within the rod slots 36 of polyaxial heads 30, the locking screw 50 can be inserted into the polyaxial head 30. In the preferred embodiment, the locking screw 50 is formed with a drive feature 51 configured to receive a screw driver and threads 52 configured to engage with the locking threads 37 of the polyaxial head 30. As the threads 52 of the locking screw 50 are threaded into the locking threads 37 of the polyaxial head 30, the locking screw 50 forces the rod 40 deeper into the rod slot 36 and against the spherical head 23 of the bone screw 20. This in turn forces the spherical head 23 of the bone screw 20 against the screw neck aperture 34 and the spherical screw head aperture 33 of the polyaxial head 30, thereby preventing the spherical head 23 of the bone screw 20 from inadvertently dislodging from the retaining tabs 35 holding the spherical head 23 within the spherical screw head aperture 33 of the polyaxial head 30 and sliding back through the horizontal screw head channel 32. The resulting force imparted by the fixing of the locking screw 50 onto the polyaxial head 30 locks the entire construct, preventing motion between the components.

Although the vertical screw head channel 31, rod slot 36, and locking threads 37 are aligned within the polyaxial head 30 in a first embodiment, this arrangement is not meant to be limiting and other configurations are possible. In a second preferred embodiment 110, as shown by at least FIGS. 18-21, the vertical screw head channel 131, rod slot 136, and locking threads 137 are not aligned within the polyaxial head 130 and instead at least the rod slot 136 is angled toward the spherical screw head aperture 133.

In the present disclosure, various features may be described as being optional, for example, through the use of the verb "may;", or, through the use of any of the phrases: "in some embodiments," "in some implementations," "in some designs," "in various embodiments," "in various implementations,", "in various designs," "in an illustrative example," or "for example;" or, through the use of parentheses. For the sake of brevity and legibility, the present disclosure does not explicitly recite each and every permutation that may be obtained by choosing from the set of optional features. However, the present disclosure is to be interpreted as explicitly disclosing all such permutations. For example, an apparatus described as having three optional features may be embodied in seven different ways, namely with just one of the three possible features, with any two of the three possible features or with all three of the three possible features.

In various embodiments elements described herein as coupled or connected may have an effectual relationship realizable by a direct connection or indirectly with one or more other intervening elements.

In the present disclosure, the term "any" may be understood as designating any number of the respective elements, i.e. as designating one, at least one, at least two, each or all of the respective elements. Similarly, the term "any" may be understood as designating any collection(s) of the respective elements, i.e. as designating one or more collections of the respective elements, a collection comprising one, at least one, at least two, each or all of the respective elements. The respective collections need not comprise the same number of elements.

In the present disclosure, all embodiments where "comprising" is used may have as alternatives "consisting essentially of," or "consisting of" In the present disclosure, any method or apparatus embodiment may be devoid of one or more process steps or components. In the present disclosure, embodiments employing negative limitations are expressly disclosed and considered a part of this disclosure.

Certain terminology and derivations thereof may be used in the present disclosure for convenience in reference only and will not be limiting. For example, words such as "upward," "downward," "left," and "right" would refer to directions in the drawings to which reference is made unless otherwise stated. Similarly, words such as "inward" and "outward" would refer to directions toward and away from, respectively, the geometric center of a device or area and designated parts thereof. References in the singular tense include the plural, and vice versa, unless otherwise noted.

The term "comprises" and grammatical equivalents thereof are used herein to mean that other components, ingredients, steps, among others, are optionally present. For example, an embodiment "comprising" (or "which comprises") components A, B and C can consist of (i.e., contain only) components A, B and C, or can contain not only components A, B, and C but also contain one or more other components.

The term "at least" followed by a number is used herein to denote the start of a range beginning with that number (which may be a range having an upper limit or no upper limit, depending on the variable being defined). For example, "at least 1" means 1 or more than 1. The term "at most" followed by a number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose limit is the second number. For example, 25 to 100 mm means a range whose lower limit is 25 mm and upper limit is 100 mm.

Many suitable methods and corresponding materials to make each of the individual parts of embodiment apparatus are known in the art. According to an embodiment of the present invention, one or more of the parts may be formed by machining, 3D printing (also known as "additive" manufacturing), CNC machined parts (also known as "subtractive" manufacturing), and injection molding, as will be apparent to a person of ordinary skill in the art. Metals, wood, thermoplastic and thermosetting polymers, resins and elastomers as may be described herein-above may be used. Many suitable materials are known and available and can be selected and mixed depending on desired strength and flexibility, preferred manufacturing method and particular use, as will be apparent to a person of ordinary skill in the art.

While various embodiments of the present invention have been disclosed and described in detail herein, it will be apparent to those skilled in the art that various changes may be made to the configuration, operation and form of the invention without departing from the spirit and scope thereof. In particular, it is noted that the respective features of embodiments of the invention, even those disclosed solely in combination with other features of embodiments of the invention, may be combined in any configuration excepting those readily apparent to the person skilled in the art as nonsensical. Likewise, use of the singular and plural is solely for the sake of illustration and is not to be interpreted as limiting.

A number of implementations have been described. Nevertheless, it will be understood that various modifications may be made. For example, advantageous results may be achieved if the steps of the disclosed techniques were performed in a different sequence, or if components of the disclosed systems were combined in a different manner, or if the components were supplemented with other components. Accordingly, other implementations are contemplated within the scope of the following claims.

The invention claimed is:

1. A pedicle implant assembly comprising:
a polyaxial head comprising a vertical screw head channel formed within a first lateral side of the polyaxial head, a spherical screw head aperture formed within a second lateral side of the polyaxial head, a horizontal screw head channel connecting between and formed continuously with both the vertical screw head channel and the spherical screw head aperture, and a pair of retaining tabs formed in exterior side walls of the polyaxial head between the horizontal screw head channel and the spherical screw head aperture, wherein the pair of retaining tabs are configured to flex outward when a head portion of a bone screw is moved between the horizontal screw head channel and the spherical screw head aperture.

2. The pedicle implant assembly of claim 1, further comprising a bone screw formed with a spherical head, a neck portion, and a threaded portion.

3. The pedicle implant assembly of claim 2, wherein the neck of the bone screw is narrower than the spherical head and threaded portion of the bone screw.

4. The pedicle implant assembly of claim 1, further comprising a screw neck aperture formed in a bottom face of the polyaxial head.

5. The pedicle implant assembly of claim 4, wherein the screw neck aperture terminates at, and is formed continuously with, a bone screw opening formed at the first lateral side of the polyaxial head.

6. The pedicle implant assembly of claim 1, further comprising a rod slot forming a U-shaped channel that is aligned with the vertical screw head channel, wherein the rod slot is configured to receive a fusion rod and guide the fusion rod into a position abutting a bone screw retained within the spherical screw head aperture.

7. The pedicle implant assembly of claim 6, wherein the U-shaped channel defining the rod slot comprises a first channel wall at the first lateral side of the polyaxial head and a second channel wall opposite the first channel wall.

8. The pedicle implant assembly of claim 7, wherein the first channel wall is formed with a first threaded top portion that is discrete from and opposes a second threaded top portion formed on the second channel wall, the first and second threaded top portions being separated by a width of the U-shaped channel.

9. The pedicle implant assembly of claim 1, wherein the polyaxial head is formed from a single block of material to provide a one-piece construction.

10. A pedicle implant assembly comprising:
a bone screw formed with a spherical head, a neck portion, and a threaded portion, wherein the neck portion of the bone screw is narrower than the spherical head and threaded portion of the bone screw; and
a polyaxial head comprising a vertical screw head channel formed within a first lateral side of the polyaxial head, a spherical screw head aperture formed within a second lateral side of the polyaxial head, a horizontal screw head channel connecting between the vertical screw head channel and the spherical screw head aperture, and a pair of retaining tabs formed in opposing exterior side walls of the polyaxial head and medially to the spherical screw head aperture, wherein the retaining tabs are configured to flex outward from the horizontal screw head channel as the spherical head of the bone screw is moved from the horizontal screw head channel into the spherical screw head aperture to reversibly secure the bone screw within the spherical screw head aperture.

11. The pedicle implant assembly of claim 10, further comprising a screw neck aperture formed in a bottom face of the polyaxial head, wherein the screw neck aperture is wider than the neck portion of the bone screw and narrower than the spherical head of the bone screw.

12. The pedicle implant assembly of claim 11, wherein the vertical screw head channel intersects with the screw neck aperture at the first lateral side of the polyaxial head and is configured to accommodate the spherical head of the bone screw.

13. The pedicle implant assembly of claim 10, further comprising a rod slot formed within the first lateral side of the polyaxial head, wherein a lateral sidewall of the rod slot is formed continuously with a lateral sidewall of the vertical screw head channel and a medial sidewall of the rod slot terminates at the screw head aperture.

14. A pedicle implant assembly comprising:
a bone screw formed with a spherical head, a neck portion, and a threaded portion, wherein the neck of the bone screw is narrower than the spherical head and threaded portion of the bone screw; and
a polyaxial head a comprising,
- a screw neck aperture formed in a bottom face of the polyaxial head,
- a vertical channel opening formed in the bottom face of a first lateral side of the polyaxial head, wherein the screw neck aperture is narrower than the spherical head of the bone screw and the vertical channel opening is wider than the spherical head of the bone screw,
- a spherical screw head aperture formed in the bottom face of a second lateral side of the polyaxial head that is at an opposite end of the polyaxial head from the first lateral side of the polyaxial head,
- a horizontal screw head channel formed continuously with, and extending away from, the spherical screw head aperture toward the vertical channel opening, and
- a rod slot forming a U-shaped channel that is configured to receive a fusion rod, the U-shaped channel comprising a first channel wall at the first lateral side of the polyaxial head and a second channel wall opposite the first channel wall, wherein the first channel wall is formed with a first threaded top portion that is discrete from and opposes a second threaded top portion formed on the second channel wall, the first and second threaded top portions being separated by a width of the U-shaped channel.

15. The pedicle implant assembly of claim 14, further comprising a pair of retaining tabs, wherein the pair of retaining tabs are formed in a wall connecting the horizontal screw head channel and the spherical screw head aperture.

16. The pedicle implant assembly of claim 15, wherein the pair of retaining tabs flex outward from the wall relative to the horizontal screw head channel and the spherical screw head aperture.

* * * * *